(12) United States Patent
Herz et al.

(10) Patent No.: US 8,530,516 B2
(45) Date of Patent: Sep. 10, 2013

(54) PROMOTING CYCLING OF APOE4 ISOFORM

(75) Inventors: Joachim Herz, Dallas, TX (US); Xunde Xian, Dallas, TX (US); Yuan Yang, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 330 days.

(21) Appl. No.: 12/962,286

(22) Filed: Dec. 7, 2010

(65) Prior Publication Data

US 2011/0136832 A1 Jun. 9, 2011

Related U.S. Application Data

(60) Provisional application No. 61/267,297, filed on Dec. 7, 2009.

(51) Int. Cl.
| | |
|---|---|
| *A01N 37/12* | (2006.01) |
| *A01N 37/44* | (2006.01) |
| *A01N 37/52* | (2006.01) |
| *A61K 31/195* | (2006.01) |
| *A61K 31/155* | (2006.01) |

(52) U.S. Cl.
USPC .......................................... 514/565; 514/634

(58) Field of Classification Search
USPC .................................................. 514/565, 634
See application file for complete search history.

*Primary Examiner* — Samira Jean-Louis
(74) *Attorney, Agent, or Firm* — Richard Aron Osman

(57) ABSTRACT

Cycling of ApoE4 isoform is promoted in a person in need thereof by contacting the person with an effective amount of a pharmaceutically-acceptable modulator of intracellular ApoE4 transport vesicle pH.

18 Claims, 1 Drawing Sheet

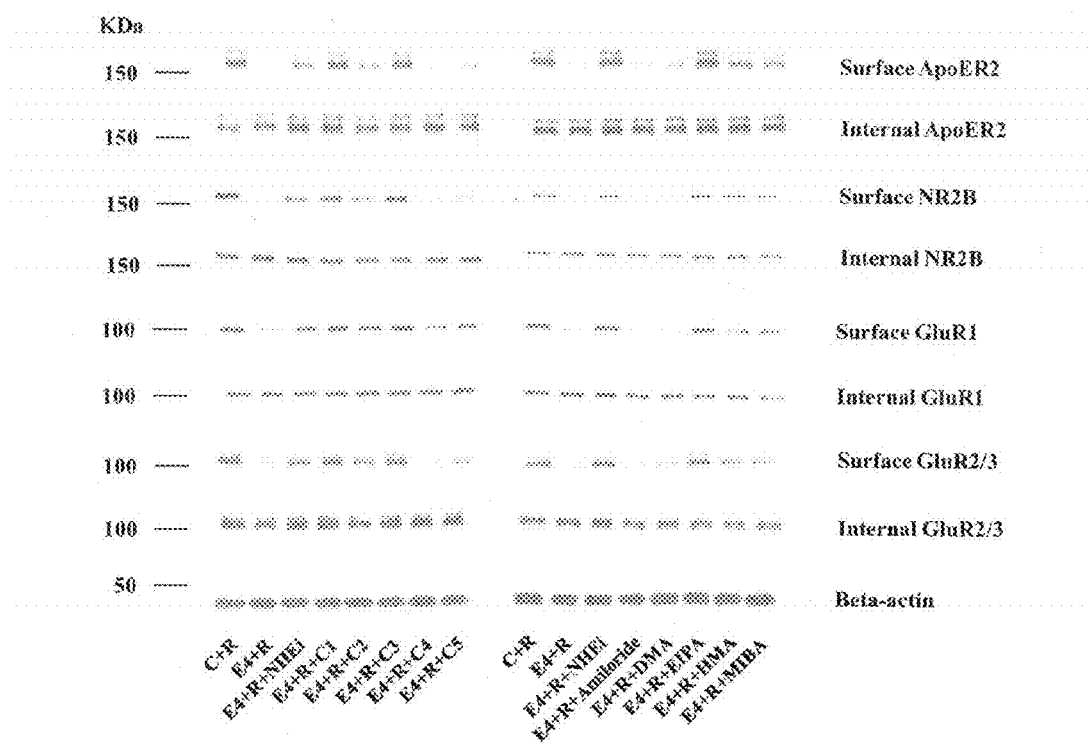

PROMOTING CYCLING OF APOE4 ISOFORM

This application claims benefit of U.S. Ser. No. 61/267,297 (Conf No. 3944), filed Dec. 7, 2009, and having the same title.

This invention was made with government support under Grant Numbers HL20948 and HL 63762; awarded by the National Institutes of Health (NIH). The government has certain rights in the invention.

The field of the invention is promoting cycling of ApoE4 isoform with modulators of intracellular vesicle pH.

INTRODUCTION

Alzheimer's disease is a prevalent neurodegenerative disorder that results in the functional and physical destruction of the brain. Apolipoprotein E4 genotype is the most important and most prevalent genetic risk factor for the clinically most relevant late-onset form of the disease.

We have shown that ApoE4 selectively impairs synaptic plasticity and NMDA receptor activation by Reelin, a regulator of brain development and modulator of synaptic strength. ApoE4 reduces neuronal surface expression of Apoer2, a dual function receptor for ApoE and for Reelin, by sequestering the receptor in intracellular compartments, thereby critically reducing the ability of Reelin to enhance NMDA receptor activity upon stimulation by glutamate. As a result, the ability of Reelin to prevent LTP suppression by extracts from Alzheimer disease afflicted human brains in hippocampal slices from knockin mice expressing the human ApoE4 isoform is severely impaired. These findings reveal an alternative mechanism by which ApoE4 can accelerate onset of dementia and neuronal degeneration by differentially impairing the maintenance of synaptic stability.

We have found that ApoE4 causes the intracellular retention of ApoE receptors, a class of signaling receptors that control synaptic plasticity in the adult brain. Treatment with an NHE inhibitor prevents the intracellular sequestration of ApoE receptors and restores normal receptor levels and function at the neuronal surface. Normalizing ApoE receptor functions in the synapse alleviates the synaptic and neuronal network dysfunction that can accelerate neuronal loss in the aging brain.

Modulators of intracellular vesicle pH like NHE inhibitors alter endosomal ApoE trafficking: the net effect is a complete reversal of the intracellular ApoE/receptor retention, and effective correction of the underlying synaptic dysfunction and prevent premature neuronal loss in ApoE4 carriers. The invention provides a rational approach to prophylactically treat anticipated Alzheimer's disease with a well tolerated, orally-available drug with minimal side effects.

SUMMARY OF THE INVENTION

The invention provides methods and compositions for promoting cycling of ApoE4 isoform in a person in need thereof. In aspect the general method comprises the step of contacting the person with an effective amount of a pharmaceutically-acceptable modulator of intracellular ApoE4 transport vesicle pH. The invention encompasses all combinations of the following embodiments.

In particular embodiments the modulator is a sodium-hydrogen exchanger (NHE) inhibitor, particularly an isoform-selective NHE inhibitor. In particular embodiments, the NHE inhibitor that is an aroylguanidine, heteroaroylguanidines, a spacer-stretched aroylguanidine, a non-acyl guanidine, or a non-guanidine NHE inhibitor.

In other embodiments, the modulator is a weak base, particularly an aminoquinoline. In particular embodiments, the aminoquinoline is a 4- or 8-aminoquinoline, preferably at a dosage subtherapeutic for rheumatoid arthritis or malaria.

In other embodiments, the modulator is a proton pump inhibitor (PPI), preferably at a dosage subtherapeutic for inhibition of gastric acid production.

In particular embodiments, the effective amount is administered chronically, such as periodically (e.g. daily) over long term (e.g. at least 6 months or life-long), such as with statins.

In particular embodiments, the person is determined (prior to, subsequent to, or as part of the method) to have a neurodegenerative disease, such as Alzheimer's disease (AD) or frontotemporal dementia (FTD), neurotrauma or pathogenically elevated plasma LDL.

The method may further comprise the step of detecting a resultant increase in ApoE4 cycling and/or trafficking (e.g. via surrogate marker like LDL decrease).

The method may further comprise the antecedent step of determining the person is an ApoE4 carrier, particularly a homozygote ApoE4 carrier. In particularly embodiments inhibitor is an NHE-6 inhibitor, which may be a direct NHE-6 inhibitor, an NHE-6 isoform selective inhibitor, and/or an indirect NHE/NHE-6 inhibitor, such as isoproterenol and 8-bromo-cAMP.

BRIEF DESCRIPTION OF THE FIGURE

FIG. 1 shows the ability of several diverse NHE inhibitors to normalize recycling of ApoE receptors; NHE inhibitor C1 is EIPA (5-(N-Ethyl-N-isopropyl)amiloride); C2-C5 are proprietary aroylguanidines and heteroaroylguanidines from Merck Serono; C is control, E4 is ApoE4, R is reelin, HMA is 5-(N,N-Hexamethylene)amiloride and MIBA is 5-(N-methyl-N-isobutyl)-amiloride.

DESCRIPTION OF PARTICULAR EMBODIMENTS OF THE INVENTION

The invention provides methods and compositions for promoting cycling of ApoE4 isoform in a person in need thereof. In aspect the general method comprises the step of contacting the person with an effective amount of a pharmaceutically-acceptable modulator of intracellular ApoE4 transport vesicle pH. Effectively the method restores ApoE4 trafficking by compensating for isoelectric retardation or delay of subcellular trafficking and retroendocytosis. The treatment effectively releases the LTP block, prevents synaptic suppression and functionally converts characteristics of APOE4 genotype to the APOE3 phenotype.

In particular embodiments the modulator is a sodium-hydrogen exchanger (NHE) inhibitor, particularly an isoform-selective NHE inhibitor. A variety of suitable NHE inhibitors are known in the art (e.g. Masereel, et al., Eu J Med Chem 38 (2003) 547-554; Morris Karmazyn, Metin Avkiran, Larry Fliegel; Springer, June 2003, "The sodium-hydrogen exchanger: from molecule to its role in disease") encompassing several classes, and we have tested and confirmed the ability of NHE inhibitors from these classes to restore ApoE and glutamate receptor recycling (see, also exemplary FIG. 1):

a) aroylguanidines such as cariporide mesilate (Hoe 642), eniporide, EMD 87580 (N-(2-methyl-4,5-bis(methylsulfonyl)benzoyl)guanidine) and related compounds, e.g. compounds of EP0758644 (E. Merck), KB-R9032 (Kanebo), BIIB 513 (Boehringer Ingelheim) and FR-183998 (Fujisawa);

b) 6-membered heteroaroylguanidines such as amiloride and derivatives such as 5-N-dimethylamiloride (DMA), 5-(N-methyl-N-isobutyl)-amiloride (MIA) and 5-(N-ethyl-N-isopropyl)-amiloride (EIPA); other heteroaroylguanidines with pyridine and quinoline heterocyclic nuclei include TY-12533 from Toa Eiyo and MS-31-038 from Mitsui Toatsu;

c) 5-membered heteroaroylguanidines include pyrrazoloylguanidines like Zoniporide (Pfizer) and indoloylguanidines like SM-20220 and SMP-300 (Sumitomo Pharmaceuticals)

d) spacer-stretched aroylguanidines like cinnamoylguanidines like S10519 (Aventis Pharma Deutschland GmbH), arylcyclopropanecarboxyl guanidines like BMX-284640 (Bristol-Myers Squibb);

e) non-acyl guanidines like T-162559 (Takeda); and f) non-gaunidine NHE inhibitors like SL 59.1227 (Sanofi-Synthelabo) and S11599 (Aventis), and squalamine.

Suitability of candidate NHE inhibitors may be screened for modulation of intracellular ApoE4 transport vesicle pH in empirically and/or in convenient ApoE cycling assays known in the art, e.g. Heeren et al. J Biol Chem 2004, 279, 55483-92.

In particular embodiments, the NHE inhibitor is isoform selective or specific. NHE shRNA inhibition data show that selective targeting of NHE-6 is sufficient to correct the ApoE4 phenotype, and restore ApoE and glutamate receptor recycling, confirming NHE-6 as a useful pharmaceutical target. Selective NHE isoform pharmaceutical targeting is readily practiced; for example, NHE5 selective inhibitors include hamaline, and N-diaminomethylene-4-(6,8-dichloro-2-methyl-1,2,3,4-tetrahydroisoquinolin-4-yl)benzenesulfonamide and its pharmaceutically acceptable salts and trifluoroacetates (e.g. Kleeman et al. US 2008/0234317). Analogously, HOE 694 is relatively selective for the NHE-2 isoform, S3226 {3-[2-(3-guanidino-2-methyl-3-oxo-propenyl)-5-methyl-phenyl]-N-isopropylidene-2-methyl-acrylamide dihydro-chloride} is a relatively potent and specific NHE-3 inhibitor, and cariporide (4-isopropyl-3-methylsulphonyl-benzoyl-guanidine methane-sulphonate) is selective NHE-1.

We have further demonstrated, that activation of beta-adrenergic receptors with isoproterenol in the presence or absence of IBMX (phosphodiesterase inhibitor), resulting in increased cAMP levels and thus PKA activation, also restores normal ApoE receptor recycling. 8-bromo-cAMP has the same effect. PKA dependent phosphorylation of the NHE cytoplasmic domain in turn results in inhibition of NHE (1 and 6). Our findings provide new applications for these and other drugs which protect against amyloid deposits, memory loss, and/or AD by directly or indirectly inhibiting NHE6, including rolipram and caffeine (a phosphodiesterase inhibitor), etc., by applying pharmaceutical intervention, including prophylactic intervention, to ApoE4 carriers, particularly E4/E4 carriers, and carriers undiagnosed with such disease or asymptomatic. See, e.g. Gong et al. J Clin Invest 114 (11) 1624-34; Cao et al. J Alzheimer's Disease 17 (2009) 681-697; Arendash et al. J Alzheimer's Disease 17 (2009) 661-680. For example, our data show very impressively that rolipram completely normalizes the recycling deficit induced by ApoE4, while it has negligible effect on altering the recycling properties of Apoer2 in the presence of ApoE3.

In other embodiments, the modulator is a weak base, particularly an aminoquinoline. In particular embodiments, the aminoquinoline is a 4- or 8-aminoquinoline. Exemplary 4-aminoquinolines include chloroquine, hydroxychloroquine or amodiaquine; and exemplary 8-aminoquinolines include primaquine, tafenoquine or pamaquine. The aminoquinoline is advantageously administered in relatively low dosages to improve tolerance, particular with chronic use, and in a preferred embodiment the dosage is subtherapeutic for rheumatoid arthritis or malaria, and/or below dosages recommended or generally considered therapeutic for prior established indications like rheumatoid arthritis or malaria. Exemplary such effective aminoquinoline daily dosages are 50 or less mg/day (e.g. 20, 10, 8, 5, 3, 2 or 1 mg/day), and are preferably submilligram daily dosages (e.g. 0.1, 0.2, 0.3, 0.5, or 0.8 mg).

In other embodiments, the modulator is a proton pump inhibitor (PPI), preferably at a dosage subtherapeutic for inhibition of gastric acid production. Exemplary such inhibitors include: omeprazole, lansoprazole, dexlansoprazole, pantoprazole, esomeprazole, and rabeprazole. The PPI is advantageously administered in relatively low dosages to improve tolerance, particular with chronic use, and in a preferred embodiment the dosage is subtherapeutic for the inhibition of gastric acid production, and/or below dosages recommended or generally considered therapeutic for prior established indications like the inhibition of gastric acid production. Exemplary such effective PPI daily dosages are 5 or less mg/day (e.g. 1, 2, 3, 4, or 5 mg), and are preferably submilligram daily dosages (e.g. 0.1, 0.2, 0.3, 0.5, or 0.8 mg). For example Prilosec (omeprazole) and Nexium (delayed release capsules of exomeprazole magnesium) are generally recommended for adults at 20 or 40 mg daily for 4 to 8 weeks for gastroesophageal reflux disease (GERD). In contrast, for treating ApoE4 individuals pursuant to the subject methods, preferred Prilosec or Nexium dosages are 0.1 to 10 mg (e.g. 0.1, 0.2, 0.3, 0.5, 0.9, 1, 2, 3, 5 or 10 mg) daily for at least 1, 2, 3, 5 or 10 years.

In particular embodiments, the effective amount is administered chronically, such as periodically (e.g. daily) over long term (e.g. at least 6 months or life-long), such as with statins.

In particular embodiments, the person is determined (prior to, subsequent to, or as part of the method) to have a neurodegenerative disease, such as Alzheimer's disease (AD) or frontotemporal dementia (FTD), neurotrauma or pathogenically elevated plasma LDL. In particular embodiments, the target person is asymptomatic patients—APO4 individuals without evidence of a neurodegenerative disorder, such as Alzheimer's disease.

The method may further comprise the step of detecting a resultant increase in ApoE4 cycling and/or trafficking (e.g. via surrogate marker like LDL decrease).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method of decreasing surface expression of ApoER2, NMDA NR2B, GluR1 and GluR2/R3 receptors in a person in need thereof, the method comprising a step of contacting the person with an effective amount of a pharmaceutically-acceptable modulator of intracellular ApoE4 transport vesicle pH and wherein the modulator is a sodium-hydrogen exchanger (NHE) inhibitor.

2. The method of claim 1 wherein the modulator is an isoform-selective NHE inhibitor.

3. The method of claim 1 wherein the modulator is an NHE inhibitor that is selected from (a) an aroylguanidine; (b) a 6-membered heteroaroylguanidine; (c) a 5-membered heteroaroylguanidine; and (d) a spacer-stretched aroylguanidine.

4. The method of claim 1 wherein the modulator is an NHE inhibitor that is an aroylguanidine selected from: cariporide mesilate (Hoe 642); eniporide; EMD 87580 (N-(2-methyl-4,5-bis(methylsulfonyl)benzoyl)guanidine); KB-R9032 (Kanebo); BIIB 513 (Boehringer Ingelheim); and FR-183998 (Fujisawa).

5. The method of claim 1 wherein the modulator is an NHE inhibitor that is a 6-membered heteroaroylguanidine selected from: amiloride; 5-N-dimethylamiloride (DMA); 5-(N-methyl-N-isobutyl)-amiloride (MIA); 5-(N-ethyl-N-isopropyl)-amiloride (EIPA); TY-12533 (To a Eiyo); and MS-31-038 (Mitsui Toatsu).

6. The method of claim 1 wherein the modulator is an NHE inhibitor that is a 5-membered heteroaroylguanidine selected from: Zoniporide (Pfizer); SM-20220 (Sumitomo Pharmaceuticals); and SMP-300 (Sumitomo Pharmaceuticals).

7. The method of claim 1 wherein the modulator is an NHE inhibitor that is spacer-stretched aroylguanidine selected from: S10519 (Aventis Pharma Deutschland GmbH); and BMX-284640 (Bristol-Myers Squibb).

8. The method of claim 1 wherein the modulator is an NHE inhibitor that is EMD 87580 (N-(2-methyl-4,5-bis(methylsulfonyl)benzoyl)guanidine).

9. The method of claim 1 wherein the person is determined to have a neurodegenerative disease selected from: Alzheimer's disease (AD) or frontotemporal dementia (FTD), neurotrauma or pathogenically elevated plasma LDL.

10. The method of claim 1 further comprising a step of detecting a resultant increase in ApoE4 cycling or trafficking.

11. The method of claim 1 wherein the effective amount is administered chronically.

12. The method of claim 1 further comprising an antecedent step of determining the person is an ApoE4 carrier.

13. The method of claim 1 further comprising an antecedent step of determining the person is a homozygote ApoE4 carrier.

14. A method of decreasing surface expression of ApoER2, NMDA NR2B, GluR1 and GluR2/R3 in a person in need thereof, the method comprising steps of:
  (a) determining the person is an ApoE4 carrier; and
  (b) contacting the person with an effective amount of a pharmaceutically-acceptable sodium-hydrogen exchanger (NHE) inhibitor selected from an aroylguanidine, a heteroaroylguanidine, and a spacer-stretched aroylguanidine.

15. The method of claim 14 wherein the NHE inhibitor is an aroylguanidine selected from: cariporide mesilate (Hoe 642); eniporide; EMD 87580 (N-(2-methyl-4,5-bis(methylsulfonyl)benzoyl)guanidine); KB-R9032 (Kanebo); BIIB 513 (Boehringer Ingelheim); and FR-183998 (Fujisawa).

16. A method of decreasing surface expression of ApoER2, NMDA NR2B, GluR1 and GluR2/R3 in a cell in need thereof, the method comprising a step of contacting the cell with an effective amount of a pharmaceutically-acceptable modulator of intracellular ApoE4 transport vesicle pH, wherein the modulator is an NHE inhibitor that is an aroylguanidine selected from: cariporide mesilate (Hoe 642); eniporide; EMD 87580 (N-(2-methyl-4,5-bis(methylsulfonyl)benzoyl)guanidine); KB-R9032 (Kanebo); BIIB 513 (Boehringer Ingelheim); and FR-183998 (Fujisawa).

17. The method of claim 16 further comprising a step of detecting a resultant increase in ApoE receptor recycling.

18. The method of claim 17 wherein the NHE inhibitor is an aroylguanidine that is EMD 87580 (N-(2-methyl-4,5-bis(methylsulfonyl)benzoyl)guanidine).

\* \* \* \* \*

UNITED STATES PATENT AND TRADEMARK OFFICE
CERTIFICATE OF CORRECTION

PATENT NO. : 8,530,516 B2
APPLICATION NO. : 12/962286
DATED : September 10, 2013
INVENTOR(S) : Joachim Herz, Xian Xunde and Yuan Yang Page 1 of 1

It is certified that error appears in the above-identified patent and that said Letters Patent is hereby corrected as shown below:

In the Specification

At Column 1, Lines 6-9, the acknowledgement of government funding should read:
--This invention was made with government support under Grant Numbers HL020948 and HL063762; awarded by the National Institutes of Health (NIH). The government has certain rights in the invention.--

Signed and Sealed this
Eleventh Day of May, 2021

Drew Hirshfeld
*Performing the Functions and Duties of the
Under Secretary of Commerce for Intellectual Property and
Director of the United States Patent and Trademark Office*